(12) United States Patent
Menard et al.

(10) Patent No.: US 9,775,573 B2
(45) Date of Patent: Oct. 3, 2017

(54) PEROPERATIVE SENSING HEAD ADAPTED TO BE COUPLED TO AN ABLATION TOOL

(71) Applicant: Centre National De La Recherché Scientifique (CNRS), Paris (FR)

(72) Inventors: Laurent Menard, Palaiseau (FR); Sebastien Bonzom, Cachan (FR); Yves Charon, Bures sur Yvette (FR); Marie-Alix Duval, Les Ulis (FR); Francoise Lefebvre-Bouvet, Palaiseau (FR); Stephane Palfi, Le Val Saint Germain (FR); Laurent Pinot, Lardy (FR); Rainer Siebert, Villepreux (FR); Stephanie Pitre, Nanterre (FR)

(73) Assignee: Centre National De La Recherche Scientifique, Paris (FR)

( * ) Notice: Subject to any disclaimer, the term of this patent is extended or adjusted under 35 U.S.C. 154(b) by 53 days.

(21) Appl. No.: 14/581,627

(22) Filed: Dec. 23, 2014

(65) Prior Publication Data

US 2015/0182177 A1    Jul. 2, 2015

Related U.S. Application Data

(63) Continuation-in-part of application No. 11/992,020, filed as application No. PCT/EP2006/066287 on Sep. 12, 2006.

(30) Foreign Application Priority Data

Sep. 13, 2005    (FR) .................................... 05 09329

(51) Int. Cl.
*A61B 6/00*    (2006.01)
*A61B 5/00*    (2006.01)
(Continued)

(52) U.S. Cl.
CPC .......... *A61B 6/4258* (2013.01); *A61B 5/0071* (2013.01); *A61B 5/0084* (2013.01);
(Continued)

(58) Field of Classification Search
CPC . A61B 1/00018; A61B 1/00114; A61B 1/117; A61B 1/00121; A61B 1/00124;
(Continued)

(56) References Cited

U.S. PATENT DOCUMENTS

| 4,870,950 A | 10/1989 | Kanbara et al. |
| 5,008,546 A | 4/1991 | Mazziotta et al. |

(Continued)

*Primary Examiner* — Timothy J Neal
(74) *Attorney, Agent, or Firm* — Foley & Lardner LLP; Nicola A. Pisano; Robert D. Ward (57) ABSTRACT

A peroperative probe for guiding a manual excision tool. The probe includes a detection head, an optical fiber for the reception and guidance of a signal emitted by radioactive tracers and fluorescent molecules in a tissue area, a photodetector for converting the emitted signal into an electrical signal, a transmitter for transmitting information carried by the electrical signal to an analysis equipment, and a fastener for attaching the probe onto the manual excision tool, so that the excision tool can be used to remove a portion of tissue from the tissue area emitting the signal.

11 Claims, 6 Drawing Sheets

(51) Int. Cl.
  *A61B 10/02* (2006.01)
  *A61B 90/00* (2016.01)
  *A61B 1/00* (2006.01)
  *A61B 17/22* (2006.01)
  *A61B 17/00* (2006.01)
  *A61B 17/32* (2006.01)

(52) U.S. Cl.
  CPC .............. *A61B 10/02* (2013.01); *A61B 90/36* (2016.02); *A61B 90/39* (2016.02); *A61B 17/22004* (2013.01); *A61B 17/320068* (2013.01); *A61B 2017/00477* (2013.01); *A61B 2090/392* (2016.02); *A61B 2090/3908* (2016.02); *A61B 2090/3937* (2016.02); *A61B 2090/3941* (2016.02); *A61B 2217/005* (2013.01)

(58) Field of Classification Search
  CPC .............. A61B 1/00126; A61B 6/4258; A61B 17/3205; A61B 19/54; A61B 5/0071
  See application file for complete search history.

(56) References Cited

U.S. PATENT DOCUMENTS

| | | |
|---|---|---|
| 5,014,708 A | 5/1991 | Hayashi et al. |
| 5,088,492 A | 2/1992 | Takayama et al. |
| 5,155,365 A | 10/1992 | Cann et al. |
| 5,170,055 A | 12/1992 | Carroll et al. |
| 5,331,961 A | 7/1994 | Inaba et al. |
| 5,377,683 A | 1/1995 | Barken |
| 5,424,546 A | 6/1995 | Okada et al. |
| 5,453,610 A * | 9/1995 | Gibbons ................ G01T 1/208 250/207 |
| 5,600,144 A | 2/1997 | Worstell |
| 5,651,783 A | 7/1997 | Reynard |
| 5,719,400 A | 2/1998 | Cherry et al. |
| 5,779,686 A | 7/1998 | Sato et al. |
| 5,811,814 A | 9/1998 | Leone et al. |
| 6,149,593 A | 11/2000 | Gonzalez-Lepera |
| 6,456,869 B1 * | 9/2002 | Raylman ................ A61B 6/425 250/370.01 |
| 6,495,834 B1 | 12/2002 | Corvo et al. |
| 6,643,538 B1 | 11/2003 | Majewski et al. |
| 8,476,594 B2 * | 7/2013 | Frach ................... G01T 1/2018 250/363.03 |
| 2002/0077643 A1 | 6/2002 | Rabiner et al. |
| 2002/0168317 A1 | 11/2002 | Daighighian et al. |
| 2003/0045780 A1 * | 3/2003 | Utsui ................ A61B 1/00167 600/182 |
| 2004/0116807 A1 | 6/2004 | Amrami et al. |
| 2005/0043617 A1 | 2/2005 | Frisch et al. |
| 2005/0181383 A1 | 8/2005 | Su et al. |

\* cited by examiner

PEROPERATIVE SENSING HEAD ADAPTED TO BE COUPLED TO AN ABLATION TOOL

FIELD OF THE INVENTION

The invention relates to assistance with the surgical treatment of biological tissue, in particular of cancerous tumours.

BACKGROUND OF THE INVENTION

Assistance with the surgical treatment of cancer is currently based on several techniques.

In a first type of technique called "pre-operative imaging techniques", before the operation the surgeon creates an image of the tissue area to be treated in order to locate, as well as possible, the tissue parts to be excised.

Pre-location of the tumour, by means of x-ray tomography or of IRM is used, for example, to obtain the precise anatomical topography of the tumorous volume and thus to choose the most appropriate surgical approaches. When coupled with mechanical stereotaxic or optical guidance, preoperative location leads to more narrowly defined and therefore less traumatising access paths, especially in the case of deep lesions.

In neurosurgery, this technique can be complemented by the use of a functional isothermal remanent magnetisation (IRM) imaging appliance, which is used, before the surgical procedure, to precisely identify the functional cerebral zoned located close to the tumour. On the basis this information, the surgeon is then able to optimise the extent of the zone to be excised while also minimising the risks of postoperative morbidity.

Preoperative imaging techniques have allowed the introduction of surgical procedures that are more precise and less invasive.

However, these techniques have limits in terms of performance and ergonomic design. In particular, these techniques are ill-suited to operations requiring location of small tumours and their metastatic disseminations if any.

In addition, the displacement of the tissue during the surgical procedure (in particular in the brain) often renders obsolete the location of lesions effected before the operation.

According to a second type of technique, the surgeon takes tissue samples during the operation, and these samples are analysed extemporaneously, so as to ensure the quality of the operating procedure of the surgeon.

These techniques, which rely upon precise anatomopathological diagnosis of the tissue samples have the advantage of being very reliable.

Such techniques are very costly however.

In addition, the time necessary to obtain a diagnosis from the samples may sometimes significantly increase the time of the surgical procedure.

Given the drawbacks associated with the preoperative imaging techniques and the tissue sampling techniques, a third type of technique called "preoperative techniques" has appeared. These techniques employ monitoring tools that are suitable of working in an operating suite, and thus of supplementing the outside imagers by helping the practitioner to determine the margins of a tumorous resection or a biopsy more precisely and in real time.

Two families of preoperative technique are currently under study. The first family of techniques, called "anatomical preoperative techniques", is based upon standard anatomical imaging systems, such as optical endoscopy systems, ultrasound echography, x-ray tomography or isothermal remanent magnetisation (IRM). The second family of techniques, called "functional preoperative techniques", are based upon the detection of signals emitted by the tissue by virtue of miniaturised systems. The signals are particles or radiation emitted by radioactive tracers or fluorescent molecules present in the tissue and specific to the tumorous lesions looked for.

According to the anatomical preoperative techniques, in order to guide his actions, the surgeon uses an anatomical imaging appliance identical in principle to those used in clinical diagnosis departments but whose characteristics, in terms of dimensions and ergonomy, have been adapted for use in operating suites.

As a complement to preoperative examination, low-field IRM and the x-ray tomography are used mainly in the operating suite in order to correct location errors associated with the displacement of the tissue during the procedure and to guide the biopsy procedures. The anatomical imaging systems are in fact used to repeat, in real time, the images created before the procedure and, as a consequence, to monitor the distortion of anatomical structures in real time. Evaluation of the preoperative IRM for surgery of the gliomas has thus shown that these techniques allow one to improve identification of the extent of the tumorous resection in relation to the procedures in which only stereotaxic guidance based on preoperative images was used.

Ultrasound echography is also used in the operating suite to assist with the surgical treatment of tumours. This technique has the advantage of being a lot less expensive and costly to put in place than low-field IRM or x-ray tomography. The principal field of application of preoperative ultrasound echography is the location of non-palpable breast tumours and tumours of the liver. More generally, this technique is particularly adapted for the precise location of deep lesions.

According to the functional preoperative techniques, the surgeon uses a miniaturised detection device that is suitable for detecting radioactive tracers or light radiation specific to the histology or the physiological or metabolic behaviour of the tumorous lesions looked for. Since the function of an organ is often disrupted before its structure, these techniques are therefore theoretically more sensitive and specific than anatomical preoperative techniques in order to distinguish the healthy tissue from the cancerous tissue.

It is thus possible to optimise identification of the extent of the tumorous resection beyond the margins identified by the preoperative examination and without having to wait for the results of extemporaneous examinations of tissue samples.

These techniques can also be used to improve the diagnosis precision of biopsies by guiding the surgeon to relevant regions of tissue to determine the histological nature of the tumour.

In general, miniaturisation of the detection devices used also leads to easier application of the functional preoperative technique in the operating suite, since it only slightly modifies the surgical protocol in relation to the more expensive and restrictive anatomical preoperative techniques.

Various counting or functional preoperative imaging devices have been developed. Some are even currently commercialised. However these devices are notable for several instrumental and methodological limits. Since there currently exists no system for functional preoperative imaging that allows the location and the simultaneous excision of the tumorous tissue. The current protocols combine two different tools which are used sequentially—the detection system (probe, microscope) and the excision tool (ultrasound aspiration device or electric lancet). This dissociation leads to correlation errors between the position of the tumour identified on the image and its actual position in the wound, and therefore reduces the precision of the excision procedure, in particular in the absence of anatomical location. The other limit of the functional preoperative devices relates their specific natures (associated with the tracers used) that is not total and therefore results in a non-negligible number of false negatives.

SUMMARY OF THE INVENTION

One aim of the invention is to allow the surgeon to perform an ablation with better precision and greater rapidity than with the devices of the prior art.

This problem is solved in the context of the present invention by using a preoperative probe to guide an excision tool in accordance with claim 1.

The detection head is adapted to be coupled to an excision tool so that the surgeon can perform detection and tumorous ablation operations in a single procedure, and with a single instrument.

More precise location of the tumorous tissue is thus achieved, because the correlation errors between the position of the tumour obtained from the signal the probe and its actual position in the operative wound are eliminated.

The ability to simultaneously measure the concentration of radioactive tracers and fluorescent molecules also allows one to benefit from the complementarity of the information acquired by these two methods, and therefore to reinforce the specificity of tumour detection.

Advantageously, a probe according to the invention measuring a signal emitted by fluorescent molecules in a tissue area, in response to a light excitation signal, also measures a light signal obtained by reflection of the light excitation signal by the tissue. The specificity is still further increased.

By virtue of the detection head, which records the signals emitted by the tissue, the surgeon can observe the treated tissue area in real time.

Advantageously, it is possible to couple the probe to a neuronavigation system so as to allow the surgeon to view the position of the probe in relation to the tumour and to the various cerebral structures identified during the preoperative IRM.

In addition, the detection head can easily be replaced by a detection head with different characteristics, in order to adapt the probe to the specific constraints of the different surgical protocols, as well as to the different signals emitted by the tissue.

The probe is particularly suitable for the surgical excision of tumours of the central nervous system, including the brain and the spinal marrow. In fact, more than for any other cancer, the precision of the surgical treatment of this pathology determines the vital and functional prognosis of the patient.

The probe can exhibit the characteristics of claims 2 to 20.

The invention also relates to a manual tool in accordance to claim 21, comprising an excision tool and a preoperative probe according to claim 1 for guiding the excision tool.

Finally, the invention relates to a system according to claim 22. This system can exhibit the characteristics of claim 23.

BRIEF DESCRIPTION OF THE DRAWINGS

Other characteristics and advantages or the invention will emerge from the description that follows, which is purely illustrative and non-limiting and should be read with reference to the appended figures, in which.

DETAILED DESCRIPTION OF THE INVENTION

Figure 1:
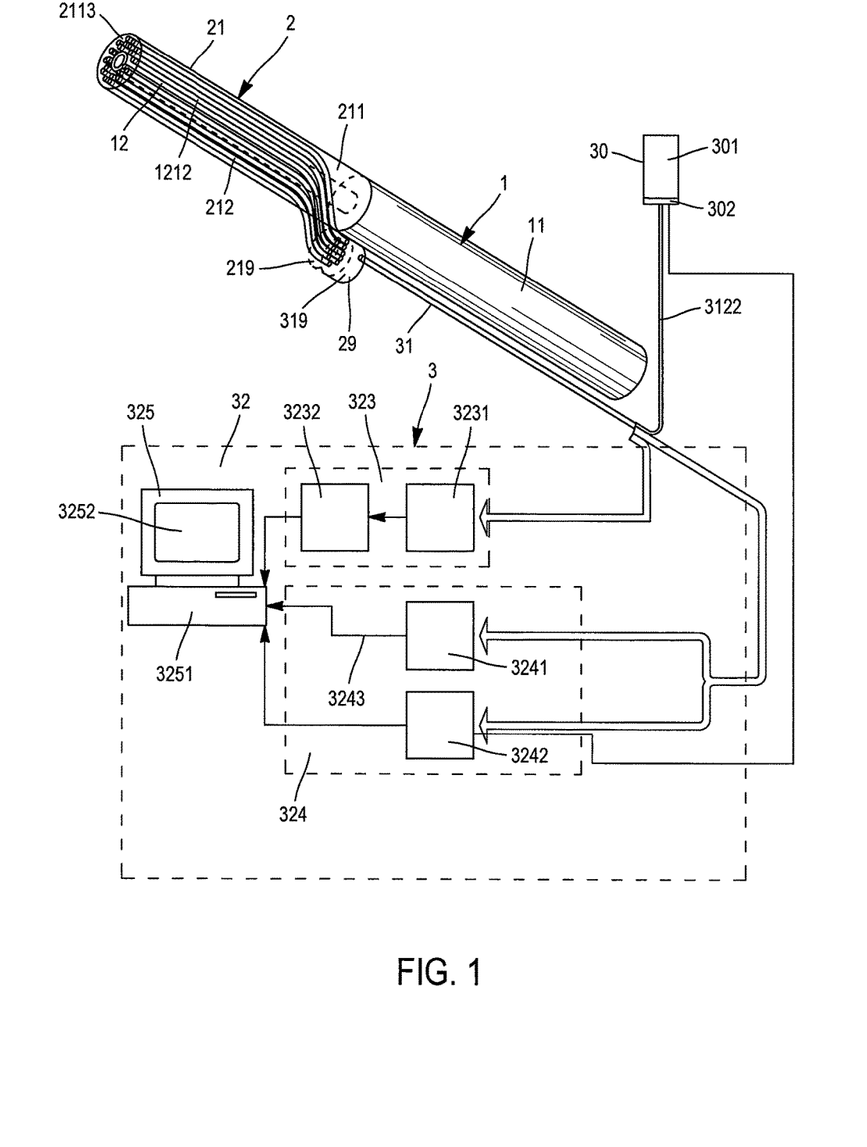
FIG. 1 schematically represents a set for the surgical treatment of biological tissue according to one embodiment of the invention, FIG. 2 schematically represents, in a front view, a detection head of a preoperative probe according to one embodiment of the invention, FIG. 3 schematically represents, in a side view and in section, a detection head of a preoperative probe according to one embodiment of the invention, FIG. 4 schematically represents, in a side view and in section, a detection head of a preoperative probe according to a variant of the embodiment of FIG. 3, FIGS. 5A and 5B schematically represent, in a side view and in section, connection components of a probe according to a first embodiment of the invention, FIG. 6 schematically represents, in a side view and in section, connection components of a probe according to a second embodiment of the invention, FIG. 7 schematically represents, in a side view and in section, connection components of a probe according to a third embodiment of the invention, FIG. 8 schematically represents, in a side view and in section, connection components of a probe according to a fourth embodiment of the invention, FIG. 9 schematically represents, in a side view and in section, connection components of a probe according to a fifth embodiment of the invention, FIG. 10 schematically represents, in a side view and in section, connection components of a probe according to a sixth embodiment of the invention, FIG. 11 schematically represents a probe according to a seventh embodiment of the invention.

In FIG. 1, the set for the surgical treatment of biological tissue represented includes an excision tool 1, a preoperative probe 2, and an analysis equipment 3.

The excision tool 1 includes a gripping part 11 and an excision part 12. The excision tool 1 is an ultrasound aspiration device for example, in particular used during the surgical treatment of gliomas in order to excise the tumorous tissue. In the case of an ultra-sound aspiration device, the excision part 12 includes a tube 1212 for the emission of ultrasound and for the aspiration of pulverised tissue.

The preoperative probe 2 includes a detection head 21 forming a part for clinical use. The detection head 21 takes the form of an end-section adapted to be fitted tightly onto the excision tool 1.

The detection head 21 includes a body 211 of generally cylindrical shape, a bundle 212 of detection optical fibres extending inside the body 211, a connection component 219 and a fastener.

The analysis equipment 3 includes a light source 30, a reusable transmission element 31 and an analysis instrument 32.

The light source 30 includes a laser or a lamp 301 and an excitation filter 302. The laser or the lamp 301 is adapted to emit light in the form of a continuous ray or light pulses of controlled length. The filter 302 is adapted to filter the light generated by the laser or the lamp 301 and to transmit an excitation signal containing photons with wavelengths adapted to excite fluorescent molecules contained in the tissue to be treated. The fluorescent molecules then emit a fluorescent light signal, whose wavelength is different from the wavelength of the excitation signal. The fluorescence is in fact electromagnetic radiation, usually in the form of visible or infrared light, coming from the emitting fluorescent molecules excited by a light excitation signal of shorter wavelength. The fluorescent radiation ceases suddenly when the excitation stops.

Figure 2:
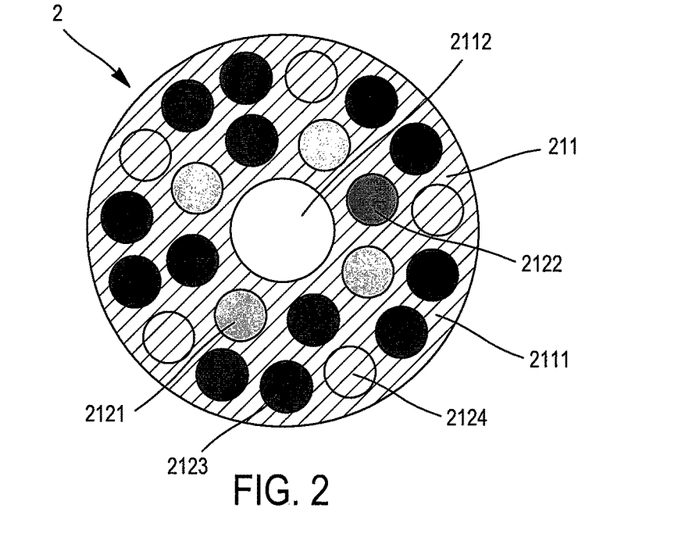
Figure 3:
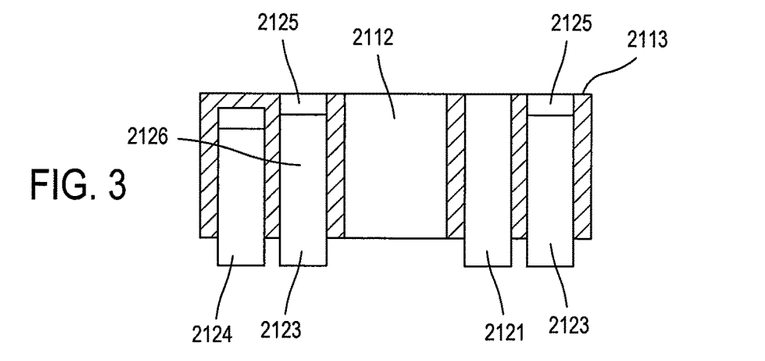

As illustrated in FIGS. 1 to 3, the detection head 21 includes a body 211 and a bundle 212 of detection optical fibres lying inside the body 211, in the longitudinal direction of the latter.

The body 211 is generally of tubular shape. The body 211 includes a cylindrical wall 2111 formed in metal, in stainless steel for example, or in any other material that is compatible with a surgical procedure, and a central channel 2112. The wall 2111 encloses the bundle 212 of detection optical fibres. The optical fibres of the bundle 212 are distributed around the central channel 2112 and lie substantially parallel to the central channel 2112.

The bundle 212 of optical fibres includes a plurality of fibres 2121 for detecting light radiation, one excitation fibre 2122, a plurality of radioactive tracer detection fibres 2123, and a plurality of control fibres 2124.

The fibres 2121, 2122 and 2123 lie between an end surface 2113 of the body 211 and the connection component 219. More precisely, the ends of the fibres 2121, 2122 and 2123 are flush with the surface 2113.

The fibres 2121 for detecting light radiation are composed of clear fibres. These fibres 2121 are adapted to receive and guide a light signal emitted by biological tissue.

The excitation fibre 2122 is also composed of a clear fibre. This fibre 2122 is adapted to guide a light excitation signal generated by the source 30 in the direction of the biological tissue, so as to excite fluorescent molecules contained in this tissue.

The radioactive tracers detection fibres 2123 include a scintillating end portion 2125 and a main clear portion 2126, with the scintillating end portion 2125 being fused to the main clear portion 2126, by heating for example. The scintillating end portion 2125 is adapted to interact with radioactive β particles ($β^+$ particles or $β^-$ particles) emitted by the tissue previously marked by radioactive tracers and to convert them into a light signal. The main portion 2126 is adapted to guide the light signal emitted by the end portion 2125.

The scintillating portion 2125 typically has a length of about 1 mm and the clear portion 2126 typically has a length of about 10 cm. The scintillating 2125 and clear 2126 portions typically have a diameter of the order of 1.5 mm.

The control fibres 2124 are identical to the radioactive tracer detection fibres 2123, except that the control fibres 2124 are rendered blind to the β particles. More precisely, the control fibres 2124 lie below the end surface 2113 of the body 211, so that the end of the control fibres 2124 is obstructed by a metal layer with a thickness of about 400 μm.

The radioactive tracers detection fibres 2123 and the control fibres 2124 are sensitive to γ radiation of 511 electron volts (eV) emitted by the tissue after the annihilation of $β^+$ particles. This γ radiation represents background noise in the detection of $β^+$ particles. The control fibres 2124 allow one to quantify the γ radiation with a view to subtracting it from the signals measured by the fibres 2123 and to thus to obtain a signal due to the $β^+$ particles only.

To allow more precise quantification of the γ radiation, the plastic scintillator may be replaced by an inorganic scintillator such as Lutetium Oxyorthosilicate doped with cerium (LSO) for example, which has a higher density and therefore a better detection efficiency for the γ radiation.

The wall 2111 in which the optical fibres 2121, 2122, 2123 and 2124 of the detection bundle 212 are buried constitutes a screen for the fibres. This screen isolates the fibres from the ambient light and any parasitic β particles that could arrive at the scintillating portions 2125 from the sides or via the rear of the fibres 2123.

Figure 4:
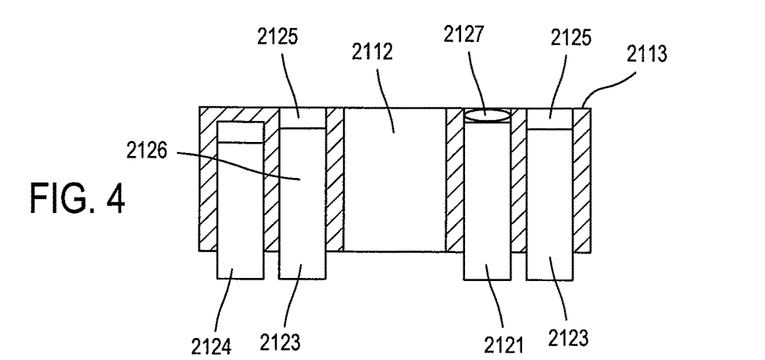

FIG. 4 illustrates a variant of the detection head 21. In this variant, the fibres 2121 and 2122 of the detection head does not extend to the end surface 2113 of the body 211. More precisely, the fibres 2121 and 2122 lie below the surface 2113. The detection head 21 includes an optical element 2127 associated with each fibre 2121 and 2122, which focuses the light coming from the tissue to the fibres 2121 and which focuses the light coming from the fibre 2122 to the tissue. Each optical element 2127 includes a microlens for example. Focusing of the incident light allows to increase the local light concentration and, as a consequence, the sensitivity of the treatment set. In addition, the collection of the light coming from the tissue with the aid of a microlens improves the spatial resolution of the treatment set.

The preoperative probe 2 further includes a fastener for attaching the probe onto the manual excision tool.

The preoperative probe 2 further includes a photo-detection unit 29 and a transmitter 31.

The photo-detection unit 29 comprises a plurality of photo-detectors 311 and comprises a battery 60 for supplying a power signal to each photo-detector 311. The battery may be located in the detection head. Alternatively the detection head is connected to an external power source which comprises the battery. Alternatively the battery is not comprised in the detection head.

Each photo-detector 311 is coupled with at least one fibre 2121 or 2123 or 2124 of the bundle 212.

Each photo-detector 311 is adapted to convert a light signal that it receives into an electrical signal representing a single pixel. Therefore, the photo-detection unit 29 produces as many pixels as many photo-detectors 311 comprised in the photo-detection unit 29.

Each photo-detector 311 may be a silicon photo-multiplier (SiPM), which is a very compact detector.

The transmitter 31 is adapted to receive electrical signals produced by the photo-detection unit 29 and transmit information carried by electrical signals to the analysis instrument.

Figure 5A:
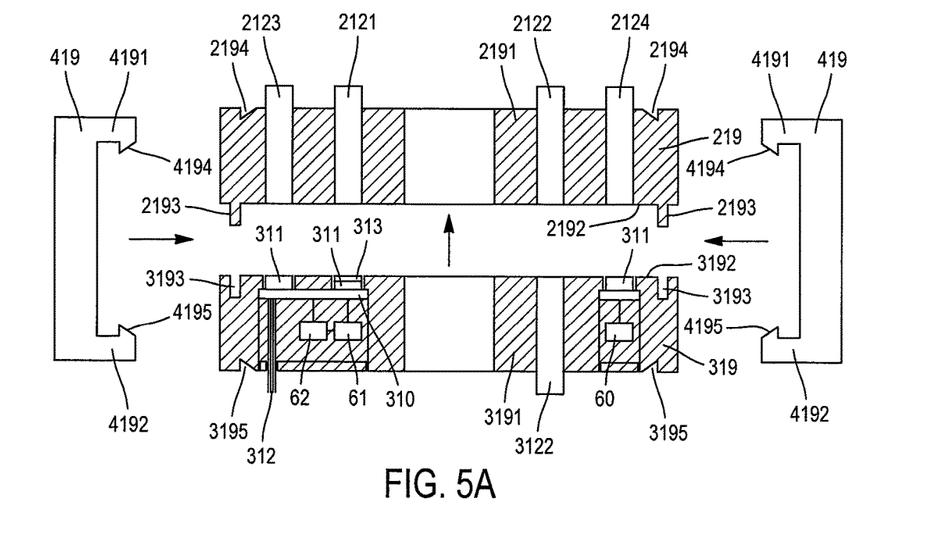
Figure 5B:
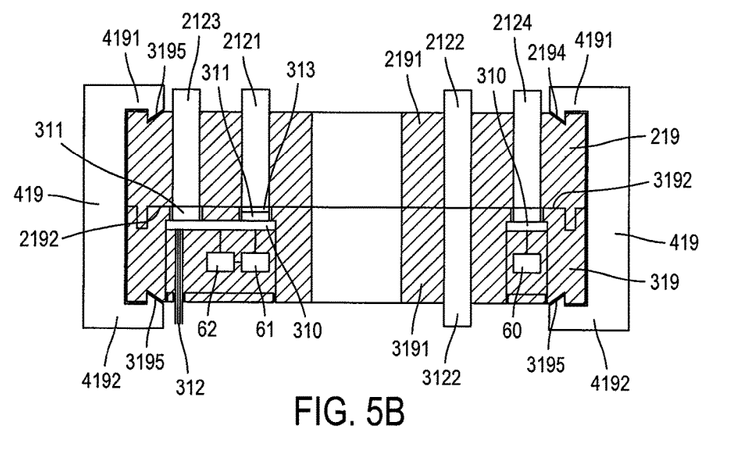

FIGS. 5A and 5B schematically represent a first embodiment for the probe 2.

In this embodiment, the preoperative probe 2 includes a detachable part which can be connected to the detection head.

The detachable part includes a connection component 319, the photo-detection unit 29 and the transmitter 31.

Connection components 219 and 319 are intended to allow connection between the detection optical fibre bundle 212 of the detection head 21 and the photo-detection unit 29 of the detachable part.

In FIG. 5A, the connection components 219 and 319 are detached from each other.

Connection component 219 includes a body 2191 in which detection fibres 2121, 2122, 2123 and 2124 are buried. The body 2191 includes a plane connection surface 2192. The ends of the fibres 2121, 2122, 2123 and 2124 are flush with the connection surface 2192.

Likewise, connection component 319 includes a body 3191 in which at least one transmission fibre 3122 is buried.

The body 3191 includes a plane connection surface 3192. The photo-detectors 311 are flush with the connection surface 3192. Besides, the end of each transmission fibre 3122 is flush with the plane connection surface 3192.

Body 2191 includes connection studs 2193 projecting from the connection surface 2192. Body 3191 includes connection orifices 3193 extending back from the connection surface 3192. The studs 2193 are adapted to be inserted into the orifices 3193 in order to orientate the connection components 219 and 319. In addition, the studs 2193 and the orifices 3193 are arranged so that when the studs 2193 are inserted into the orifices 3193, connection surface 2192 comes into contact with connection surface 3192, and the end of fibre 2121 comes into contact with the end of fibre 3122, in order to connect the fibres together. The ends of each fibre 2121, 2122 and 2124 also come into contact with the top surface of each photo-detector 311.

The probe can also include locking components 419 intended to hold the connection components 219 and 319 in engagement. Each locking components is U-shaped and includes two branches 4191 and 4192. At each free end, each branch 4191 and 4192 respectively has a projection 4194 and 4195.

Each of the connection components 219 and 319 respectively includes notches 2194 and 3195.

The locking components 419 are adapted to hug together the connection components 219 and 319 when they are in mutual engagement. To this end, the components 219 and 319 are inserted between the branches 4191 and 4192 of the locking components 419. The presence of the projections 4194 and 4195 causes the separation of the branches 4191 and 4192 by elastic deformation. The projections 4194 and 4195 are then adapted to be inserted into the notches 2194 and 3195 by elastic return of the branches 4191 and 4192.

Each photo-detector 311 of the photo-detection unit 29 is coupled to a single fibre 2121 or 2123 or 2124. As an example, FIG. 5A shows a first photo-detector coupled with a fibre 2123, a second photo-detector coupled with a fibre 2121, and a third photo-detector coupled with a fibre 2124.

In this embodiment, the transmitter 31 comprises an integrated circuit 310 and a transmission cable 312.

The integrated circuit 310 is buried in component 319 between the transmission cable 312 31 and the photo-detection unit 29. Although not entirely visible on FIGS. 5A and 5B, the integrated circuit 310 is connected to each photo-detector of the photo-detection unit 29.

The integrated circuit 310 is adapted to receive the electrical signal delivered by each photo-detector of the photo-detection unit 29. Each received electrical signal is routed by the circuit on a respective conducting wire of the transmission cable 312. Thus, the transmission cable 312 can carry a plurality of electrical signals representing a plurality of pixels.

The integrated circuit 310 can further comprise (or be coupled to): at least one temperature sensor 61 (for example one temperature sensor per photo-detector) and a power management circuit 62.

Each temperature sensor 61 is adapted for sensing a temperature of at least one of the photo-detectors 311.

The power management circuit 62 is connected to the battery 60 and to each temperature sensor 61. The power management circuit 62 is adapted to adjust the power signal supplied by the battery 60 to a given photo-detector 311, based on the temperature sensed by the temperature sensor 61 associated with the given photo-detector 311. For instance, a voltage supplied by the battery 60 to the photo-detectors 311 can be adjusted so as to stabilize the behaviour of the photo-detectors over time.

The transmission cable 312 includes multiple electrical conducting wires. The transmission cable 312 is connected to the analysis instrument 32. The transmission cable 312 typically has a length of 2 meters, to route the electrical signals coming from the detection head 21 to the analysis equipment 32 located outside the operative field.

In FIG. 5B, the connection components 219 and 319 are brought into mutual engagement and the locking components 419 hold the connection components 219 and 319 in mutual engagement. Under this configuration of the probe the end of fibre 2123 is in contact with the first photo-detector, the end of fibre 2121 is in contact with the second photo-detector, and the end of fibre 2124 is in contact with the third photo-detector.

As can be seen in FIG. 1, the single-use detection head 21 is adapted to be attached in a detachable manner to the excision tool 1. To this end, the excision part 12 of the tool 1 is adapted to be inserted into the detection head 21. More precisely, the aspiration tool 1212 of the excision tool 1 is adapted to be inserted into the channel 2112 of the detection head 21 so that the aspirating end of the aspiration tool 1212 is flush with the end surface 2113 of the detection head 21.

Secondly, the connection components 219 and 319 are adapted to be brought into mutual engagement in order to couple the bundle 212 of detection optical fibres optically to the photo-detection unit 29. The connection components 219 and 319 are detachable connection components. This allows easy manual connection and disconnection.

The single-use detection head 21 can therefore be replaced easily by another head.

When the connection components 219 and 319 are brought into engagement, the excitation fibre 2122 of the detection head is connected to the transmission fibre 3122 of the transmission cable 312.

The transmission fibre 3122 is connected firstly to the source 30 and secondly to the excitation fibre 2122 so as to guide the excitation radiation, emitted by the source 30, to the tissue to be treated.

The analysis equipment 32 includes a first acquisition unit 323, a second acquisition unit 324 and a PC 325.

The wires of the transmission cable 312 carrying information from the detectors coupled to fibres 2123 and fibres 2124 are connected to the first acquisition unit 323.

The first acquisition unit 323 includes pre-amplification electronics 3232 and amplification electronics 3233.

The pre-amplification electronics 3232 and the amplification electronics 3233 are adapted to integrate and then to amplify the electrical signals carried by the transmission cable 312. The unit 323 then transmits the analogue signals to the PC 325 for their digitisation and their treatment.

The wires of the transmission cable 312 carrying information from the detectors coupled to fibres 2121 are connected to the second acquisition unit 324.

The second acquisition unit 324 includes a first conversion electronics unit 3241 and a photon counting electronics unit 3242.

The first conversion electronics unit 3241 is adapted to integrate, amplify and convert the analogue electric signals received from the transmission cable 312 31 in digital signals, in order to allow direct transfer to the PC 325 via a USB cable 3243.

The photon counting electronics unit 3242 is suited to count and measuring the time of passage of fluorescence photons based on the electrical pulses carried by the transmission cable 312. The time of passage is measured with respect to the excitation time of tissue by source 30.

The photo counting unit 3242, is connected to the PC 325, for instance via a USB cable, in order to allow direct transfer of the data counted and measured by the photon counting unit to the PC 325.

The PC 325 includes a digitising and calculating unit 3251 and a display screen 3252. The digitising and calculating unit 3251 is adapted to receive and to process the signals generated by units 323 and 324. The digitising and calculating unit 3251 is also adapted to control the display screen 3252.

The use and the operation of the surgical treatment set that has just been presented will now are described.

Before an operation, the surgeon chooses a detection head 21 that is suitable for the operative wound and for the type of tumour to be treated.

The surgeon attaches the detection head 21 to the excision tool 1 by inserting the aspiration tool 1212 into the channel 2112 of the detection head 21.

Then the surgeon connects the fibre bundles 212, 312 together by means of the connection components 219 and 319.

During the operation, the surgeon performs the excision of a visible part of the tumour.

Next, the surgeon inserts the end of the probe 2 into the operative wound. More precisely, the surgeon positions the probe 2 so that the end surface 2113 of the detection head 21 is positioned facing a tissue zone to be treated. The surgeon moves over the operative wound by means of the detection head 21 and positions the detection head 21 in a plurality of successive positions. For each position of the head 21, the surgeon creates a mapping of the signals emitted from the tissue zone facing the end surface 2113. For each position of the detection head 21, the acquisition time of the mapping does not exceed a few seconds.

The preoperative probe allows firstly to detect particle-emitting radioactive tumorous tracers.

When a $\beta$ particle emitted by the tissue area is received by one of the fibres 2123, the scintillating portion 2125 of the fibre 2123 generates a light signal (a pulse) that is guided by the clear portion 2126 of the detection fibre 2123.

The light signal is guided to a corresponding photo-detector. The photo-detector generates an electrical signal (electrical pulse), whose amplitude is proportional to the intensity of the light signal and represents a pixel.

The electrical signal is transmitted via the integrated circuit 310 to a corresponding wire of the transmission cable 312 31, which transmits the electrical signal to the acquisition unit 323.

The acquisition unit 323 supplies the number associated with the fibre 2123 affected by the $\beta$ particle or a gamma radiation, and the energy deposited in the scintillating portion 2125. The acquisition unit 323 amplifies and digitises the electrical signals generated by the photo-detectors 311 coupled to the fibres 2123, and transmits the amplified signals to the digitising and calculating unit 3251.

In addition, the control fibres 2124 are sensitive only to the $\gamma$ radiation generated by the tissue.

A given control fibre 2124 guides a second light signal to another photo-detector. This photo-detector generates a second electrical signal (electrical pulse) that is proportional to the intensity of the second light signal and represents another pixel.

The second electrical signal is also transmitted by a dedicated wire of the transmission cable 312 31 to the acquisition unit 323.

The $\gamma$ radiation resulting from annihilation of the $\beta+$ particles in the tissue, represents background noise for the process of locating tumorous lesions in the operative wound. These signals can in fact come from regions, specific or non specific to attachment of the $\beta+$ tracer, that are very distant from the tissue zone analysed by the probe.

In order to distinguish the $\gamma$ signals from the $\beta+$ signals, the surgical treatment set has the following characteristics.

According to a first characteristic, the scintillating portions 2125 of the fibres 2123 are formed from a plastic material, which are not very sensitive to the high-energy $\gamma$ radiation. In fact the plastic material has a low density (typically 1.05 g/cm3 and is composed of elements with a low atomic number (6 at most for Carbon). The simulated $\gamma$ efficiency of a scintillating plastic fibre, 2 mm in diameter and 1 mm in length, located to 0.1 mm from a one-off source of $^{18}F$, is thus about 300 impacts per second per microCurie (cps/$\mu$Ci) against a $\beta+$ efficiency of $1.7.10^4$ cps/$\mu$Ci in the same configuration.

In the case of treatment of a cerebral tumour, this radiation can come from the whole of the brain however. The contribution of the $\gamma$ background noise to the $\beta+$ signal can therefore become very high, despite the intrinsic low sensitivity of the plastic material constituting the scintillating portion.

According to a second characteristic, the digitising and calculating unit 3251 is adapted to select the signals that it receives according to the energy of the particle that has interacted with the scintillating portion. The theoretical study of the energy spectrum of the $\gamma$ radiation that has interacted with the scintillating portion in fact shows that 40% of the $\gamma$ detected radiation generates an energy of between 0 and 1000 keV, while the energy distribution of the $\beta+$ articles is between 0 and 500 keV.

The digitising and calculating unit 3251 is therefore adapted to select only the signals whose energy is greater than a threshold of between 50 and 100 kiloelectronvolt (keV).

According to a third characteristic, each radioactive tracer detection fibre 2123 is associated with a control fibre 2124. The control fibres 2124 are sensitive to the $\gamma$ radiation but are insensitive to the $\beta+$ particles. The unit 3251 is adapted to subtract, from the count corresponding to the signals generated by a radioactive tracer detection fibre 2123, the $\gamma$ count corresponding to the signals generated by the associated control fibre 2124, in order to obtain a measurement of the $\beta+$ signal only.

It will be noted in this regard that several radioactive tracer detection fibres 2123 can be associated with a single control fibre 2124 so as to optimise the portion of the detection surface 2113 sensitive to the $\beta$ articles.

The digitising and calculating unit 3251 is adapted to compare the count of the pulses corresponding to the radioactive tracer concentration measures at the fibres 2123 of the detection head 21 with a reference count measured previously in a zone of the operative wound composed of healthy tissue only.

When the difference between the measured count and the reference count is greater than a threshold standard deviation (greater than 3 for example) then the unit 3251 will identify the tissue area as tumorous.

The digitising and calculating unit 3251 commands the screen 3252 so that the latter displays a mapping of the tissue area on which the number of $\beta$ particles detected by each fibre 2123 is indicated.

The surgeon may thus view an image of the treated tissue zone on the screen 3252 in real time, which indicates the distribution of the radioactive tracer concentration at the fibres 2123 of the detection head 21.

The preoperative probe is also used for tumorous tissue detection by fluorescent optical techniques.

Thus, the clear fibres 2121 receive the fluorescent radiation emitted by fluorescent molecules present in the tissue after the molecules have been excited by a light excitation signal conducted by the fibre 2122 to the tissue. The light signal containing the fluorescent light radiation is guided by the clear fibres 2121 to a photodetector 311 of the photo-detecting unit through a filter 313 arranged between the proximal end of the fibre and the photo-detector. The filter 313 selects a specific wavelength or range of wavelengths from the light signal guided by the optical fibre 2121 and produces a filtered fluorescence signal, wherein the photo-detector is arranged to receive the filtered signal.

The photo-detector generates an electrical signal whose amplitude is proportional to the intensity of the filtered fluorescence signal. This electric signal is received firstly by the acquisition unit 324.

The unit 3241 supplies the intensity of the fluorescence light corresponding and the number associated with the fiber 2121, which collected the fluorescence light. The conversion electronics unit 3241 digitises the filtered fluorescent signal and transmits the digitised signal to the digitising and calculating unit 3251. The unit 3242 supplies the number of photons of the filtered fluorescent signal and measure their time of passage; the unit 3242 then transfers counted data and measured times directly to the unit 3251.

The digitising and calculating unit 3251 is adapted to compare the count of the radiation detected by the fibres 2121 with a reference count, measured previously in a zone of the operative wound composed of healthy tissue only. When the difference between these counts is greater than a predetermined threshold (the count has a standard deviation greater than 3 in relation to the reference count for example), the unit 3251 will identify the tissue area as tumorous.

In addition, the digitising and calculating unit 3251 is adapted to compare the intensity of the fluorescent radiation in a selected and adjustable range of wavelength of the fluorescence spectrum detected by the fibres 2121 with a reference intensity measured previously in a zone of the operative wound composed of healthy tissue only. For example, when the "red" contribution of the spectrum (wavelengths between 600 and 700 nm) is greater by more than 100% in relation to the reference spectrum, the unit 3251 will identify the tissue area as tumorous.

In addition, the digitising and calculating unit 3251 is adapted to calculate the decay time of the fluorescence from the signals of the unit 3242 and to compare these with reference decay times measured previously in a zone of the operative wound composed of healthy tissue only. When at least one of the measured decay times has a standard deviation that is greater by 50% in relation to the reference time, the unit 3251 will identify the tissue area as tumorous.

Finally, the digitising and calculating unit 3251 is adapted to process in combination the various data produced by the devices 3233, 3241, 3242 and 3223. The identification of tumorous tissue is thus based on complementary data and leads to results that are more reliable than with independent use of the different data.

In particular, for several measurements based on different independent parameters from the same tissue area indicating a tumorous zone without however exceeding the thresholds specified for a reference zone, the unit 3251 will identify the zone as tumorous. In the opposite case, in which a meaningful measurement (standard deviation greater than 3) is not confirmed, or if it is contradicted by other measurements, then the unit 3251 will not propose excision of the corresponding tissue.

The processing unit 3251 controls the screen 3252 so that the latter displays several two-dimensional graphs each representing the tissue area. The first graph indicates the count of the β tracers at each fibre 2123.

The unit 3251 may command the screen 3252 to present a second graph representing the intensity of the fluorescent radiation according to the wavelength of the radiation. Beforehand, the surgeon will have chosen a wavelength window and, in this second graph, the screen 3251 will display only the intensity of the fluorescent radiation at the fibres 2121 whose wavelengths are between the lower limit and the upper limit of the window chosen by the surgeon.

The unit 3251 also controls the screen 3252 so that the screen 3252 displays a third graph representing the decay time of the radiation emitted by the fluorescent molecules detected at the fibres 2121.

The surgeon may thus view several mappings of spatial distributions of measured intensities and of the parameters specific to the treated tissue zone on the screen 3252, in real time.

The screen 3252 may simultaneously display several measured mappings and superimposed these on each other.

The screen 3252 may also display a table summarising the results of the measurements taken individually and offer conclusions to the surgeon.

According to the mapping or mappings displayed by the screen 3252, the surgeon may decide whether to excise the tissue zone by means of the excision tool 1.

Figure 6:
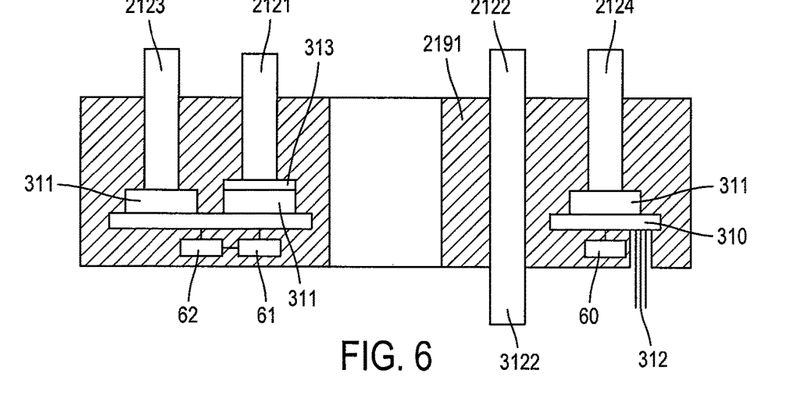

A second embodiment of the probe 2 is depicted on FIG. 6.

This second embodiment differs from the first embodiment shown on FIGS. 5A and 5B in that the photo-detection unit 29, the filter 313, the integrated circuit 310 and the transmitter 31 are buried in the detection head, rather than in a detachable part connectable to the detection head.

Figure 7:
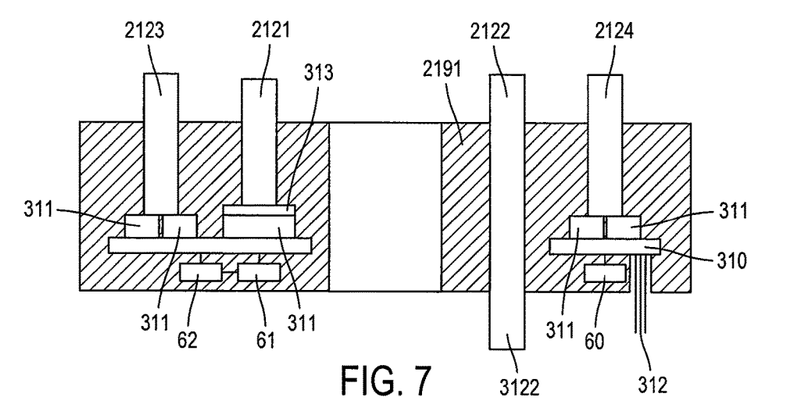

A third embodiment of the probe 2 is depicted on FIG. 7.

This third embodiment differs from the second embodiment in that many photo-detectors can be coupled to one same fibre, for instance a fibre 2123 and/or a fibre 2124.

In the particular example depicted on FIG. 7, two photo-detectors 311 are arranged in the body of the probe and put in contact with the proximal end of a fibre 2123, and two other photo-detectors 311 are arranged in the body of the probe and put in contact with the proximal end of a fibre 2124. Each photo-detector produces a distinct electrical signal representing a pixel.

Such arrangement is advantageous in that most of photo-detectors generate a noise, said "dark noise". Since dark noises generated by two distinct photo-detectors are not correlated, the influence of said dark noises can be removed by detecting in coincidence both electrical signals produced by the two photo-detectors. Thus, the detection threshold may be very low and the beta sensitivity is increased.

Of course, coupling more than one photo-detector with one single fibre can also be included in the first embodiment.

Figure 8:
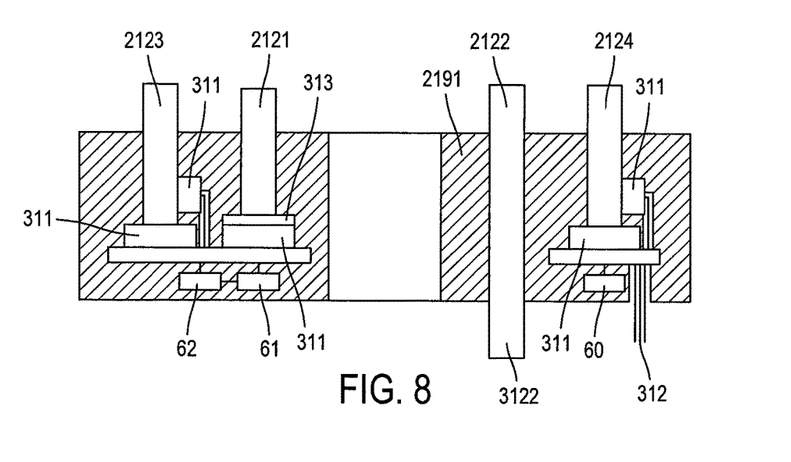

A fourth embodiment of the probe 2 is depicted on FIG. 8.

As in the third embodiment, a plurality of photo-detectors can be coupled with one same fibre. However, at least one photo-detector of this plurality is arranged to contact with the proximal end of the same fibre, whereas at least one other photo-detector is arranged to contact with a lateral side of the same fibre. This arrangement improves collection of light by the plurality of photo-detectors.

Figure 9:
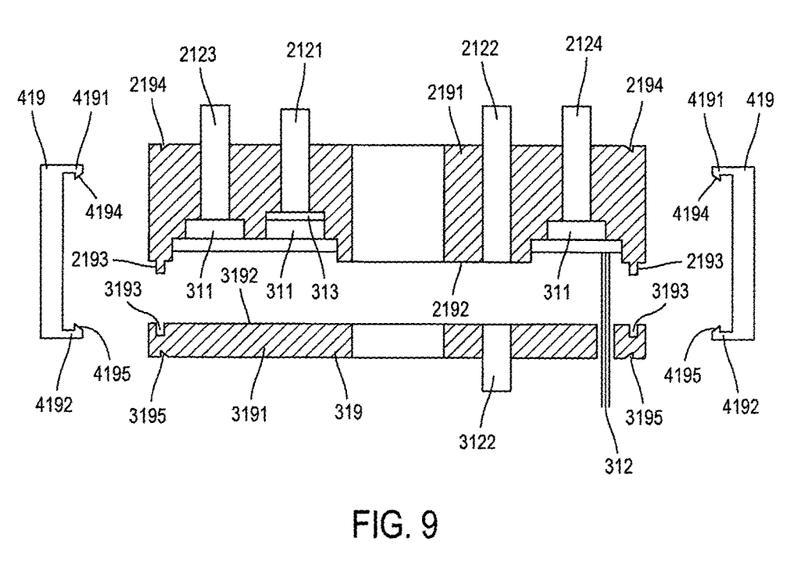

A fifth embodiment of the probe 2 is depicted on FIG. 9.

This fifth embodiment differs from the first embodiment in that the detection head comprises the photo-detecting unit and the integrated circuit 310, whereas the detachable part comprises a portion of transmission fibre 3122.

It can be noted that each fibre 2122 and a corresponding fibre 3122 can be distinct (as shown in the first and fifth embodiment) or parts of a same fibre (as shown in the second, third and fourth embodiments).

In all variants of the treatment set described above, the transmitter 31 comprises a cable connected to the analysis instrument.

Figure 10:
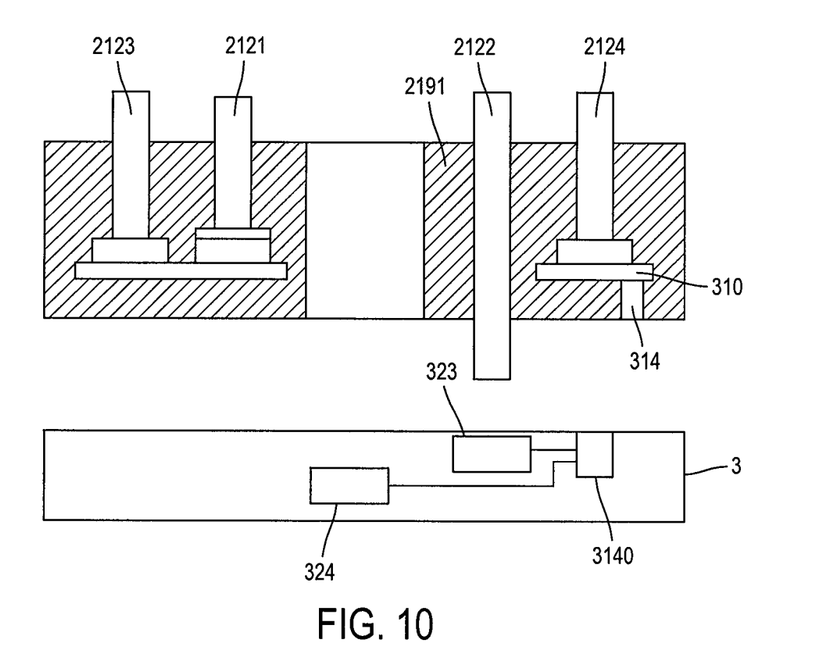

In another embodiment illustrated in FIG. 10 referred to as "wireless embodiment", the transmitter comprises a wireless communication module 314 connected to the integrated circuit 310. The wireless communication module 314 is adapted to convert an electrical signal received from the integrated circuit 310 into a radio signal. In the wireless embodiment, the light source 30 can be included in the detection head. In this embodiment, the light source 30 may comprise at least one LED. The light source 30 may include at least three LED in order to compute a 3D position.

The analysis instrument comprises a wireless communication module 3140 adapted to receive the radio signal and converts it into an electric signal and transmits the electric signal the to the PC 325.

Both wireless communication modules can support various wireless communication protocols: Wi-Fi, Bluetooth, etc.

Figure 11:
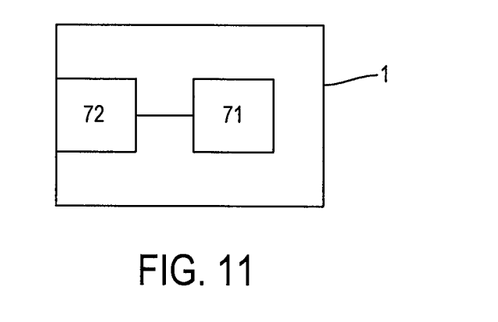

Now referring to FIG. 11, the probe can also comprise a position transmitter 72 for transmitting the 3D position of the probe to an position analysis equipment (for example to the analysis instrument 32, or to another equipment).

In another embodiment, the position transmitter comprises a luminescent source, such as a LED, and the position analysis equipment comprises a camera for capturing an image showing light emitted by the luminescent source, and a processor for estimating the position of the probe based on the captured image.

In still another embodiment, the luminescent source is replaced by a predetermined marker applied on a surface of the probe and known by the position analysis equipment. Therefore, the processor can detect the pattern of the marker in an image captured by the camera and estimate the position of the probe based on the pattern.

The position sensor 71 may be located in the detection head, or located in a detachable navigation module connectable to the detection head.

The position sensor 71 may be included in any embodiment described upwards.

The 3D localisation of the probe allows correlating more accurately the position of the excision tool and the image of the distribution of the radioactive or fluorescent signals produced by the optical fibres. In practice, because the 3D position in space of the detection optical fibers is measured through the position sensor, the true position of tumor tissue identified from the radioactive and/or fluorescence signals detected by the optical fibers is also determined. Thus, the surgeon can put the tip of the excision tool perfectly on contact with the tumor areas in order to remove them. The 3D localisation also allows to check that the overall surgical wound has been explored by recording the positions in space already traveled by the probe.

It will be noted that the number and arrangement of the optical fibres in the detection head 21 can easily be modified, so as to meet the constraints of the different surgical protocols.

The probe 2 may be rendered more versatile by providing a range of interchangeable detection heads 21 that satisfy the various specifications (compactness, sensitivity, resolution, etc.).

It is thus possible to provide a detection head that included only on clear fibre 2121 and one excitation fibre 2122 for detection of the fluorescent molecules present in the tissue.

It is also possible to provide a detection head that includes only one radioactive β tracer detection fibre 2123 and one control fibre 2124. This type of detection dead is particularly suitable for surgical procedures that require extreme compactness of the probe, such as excision procedures under endoscopy or biopsies.

At the other extreme, it is possible to provide a detection head that includes several concentric layers of detection fibres 2121 and 2123, used to perform mapping of the spatial distribution of the radioactive tracers and of the light radiation in a field of view of the order of 2 square centimeters ($cm^2$). This type of detection head is suitable for surgical procedures that call for rapid exploration of the operative wound, or for operations that are limited by high non-specific fixing of the radioactive tracers.

In contrast to a counting probe, the option to create a mapping of the tissue area to be treated in fact allows one to distinguish the tumorous signals specific to the background noise, and therefore to improve the signal to noise ratio, which can be badly affected by the heterogeneity of the tracer fixing in the tissue surrounding the lesion.

Between these two extreme configurations just presented, detection heads with intermediate arrangements of fibres, in terms of number and positioning, may also be envisaged.

Advantageously, it is possible to combine and sum the data coming from each fibre in a single signal. The sum is then used as a single mono-pixel detector, in such a way that the probe has a better sensitivity for more rapid identification of the zones to be treated.

The treatment set just described allows simultaneous measurement of the concentration of radioactive tracers and the fluorescent molecule distribution. This association is used to increase the complementarity of the histological, metabolic and molecular data supplied by these different measurements, and thus to increase the efficiency of preoperative detection of tumours.

The probe just described is of small dimensions and is easy to manipulate, thus allowing access to narrow regions of operative wounds (cavities of the order of 3 to 5 cm for cerebral tumours for example).

In addition, the probe allows precise and rapid location of the zones of tissue to be excised.

Coupling with the excision tool in fact allows the surgeon to view, in real time, a mapping of the tissue area located close to the excision tool, and therefore to perform a more precise and rapid excision of the tumorous tissue in a single procedure, having first marked it out.

Finally, the probe allows more specific detection of the tumours than with the techniques of the prior art. In fact, combining the detection of several types of tracer allows one to supply more precise and reliable information on the nature of the tissue treated.

A probe according to the invention, measuring a signal emitted by fluorescent molecules in a tissue area, in response to a light excitation signal, advantageously also measures a light signal obtained from the reflection of the light excitation signal by the tissue.

In the foregoing developments, a bundle of micro-optical fibres of very small diameter can naturally replace each optical fibre described.

The invention claimed is:

1. A preoperative probe for use with an analysis equipment for guiding a manual excision tool, comprising:
a single-use detection head comprising a first body having a first optical fiber for the reception and guidance of a signal representative of both beta and gamma particles emitted by radioactive tracers in a tissue area, a second optical fiber for reception and guidance of a signal representative of gamma radiation only, and a first planar connection surface having a connection stud, the first and second optical fibers each having an end disposed flush with the first planar connection surface; and
a reusable detachable part comprising a second body having a second planar connection surface and a connection orifice, a first photo-detector for converting the signal guided by the first optical fiber into a first electrical signal, a second photo-detector for converting the signal guided by the second optical fiber into a second electrical signal, and an integrated circuit coupled to the first and second photo-detectors to output information for processing to the analysis equipment, each of first and second photo-detectors disposed flush with the second planar connection surface;
a transmitter for transmitting the information output by the integrated circuit to the analysis equipment; and
locking component for removably coupling the second body to the first body so that the first and second planar surfaces mate, the first optical fiber is disposed adjacent to the first photo-detector, the second optical fiber is disposed adjacent to the second photo-detector and the connection stud and the connection orifice interengage.

2. The probe according to claim 1, wherein the transmitter comprises a wireless communication module.

3. The probe according to claim 1, wherein the transmitter comprises a transmission cable coupled to the reusable detachable part.

4. The probe according to claim 1, wherein at least one of the first and second photo-detectors comprises a silicon photomultiplier.

5. The probe according to claim 1, wherein the detection head comprises a handpiece configured to be manipulated by a clinician.

6. The probe according to claim 5, wherein handpiece is configured to receive an excision tool.

7. The probe according to claim 1, further comprising a temperature sensor for sensing a temperature of one of the first and second photo-detectors.

8. The probe according to claim 7, further comprising a battery for supplying a power signal to the first and second photo-detectors and the integrated circuit is configured to adjust the power signal based on the temperature sensed by the temperature sensor.

9. The probe according to claim 1, wherein the transmitter is arranged to transmit information carried by the first electrical signal and the second electrical signal to the analysis equipment.

10. The probe according to claim 1, further comprising a third photo-detector, wherein the first photo-detector comprises a surface in contact with an end of the first optical fiber, and the third photo-detector comprises a surface in contact with a side of the first optical fiber or the end of the first optical fiber.

11. The probe according to claim 1, further comprising a third photo-detector, wherein the second photo-detector comprises a surface in contact with an end of the second optical fiber, and the third photo-detector comprises a surface in contact with a side of the second optical fiber or the end of the second optical fiber.

* * * * *